United States Patent [19]

Evard

[11] Patent Number: 5,242,396

[45] Date of Patent: Sep. 7, 1993

US005242396A

[54] DILATATION CATHETER WITH REINFORCING MANDREL

[75] Inventor: Philip C. Evard, Palo Alto, Calif.

[73] Assignee: Advanced Cardiovascular Systems, Inc., Santa Clara, Calif.

[21] Appl. No.: 810,387

[22] Filed: Dec. 19, 1991

[51] Int. Cl.⁵ .......................................... A61M 25/00
[52] U.S. Cl. ..................................... 604/96; 606/194
[58] Field of Search .................. 600/18; 128/656–658; 604/96–103; 606/191, 192, 194

[56] References Cited

U.S. PATENT DOCUMENTS

| | | | |
|---|---|---|---|
| 4,597,755 | 7/1986 | Samson et al. | 604/96 |
| 4,616,653 | 10/1986 | Samson et al. | 606/192 |
| 4,771,778 | 9/1988 | Mar | 606/192 |
| 5,040,548 | 8/1991 | Yock | 128/898 |

Primary Examiner—C. Fred Rosenbaum
Assistant Examiner—Corrine Maglione
Attorney, Agent, or Firm—Crosby, Heafey, Roach & May

[57] ABSTRACT

A dilatation catheter for angioplasty procedures having inner and outer tubular members with a reinforcing mandrel fixed within the annular lumen between the the inner and outer tubular members. The catheter is adapted for use with a guidewire having an OD of not more than 0.014 inch (0.356 mm), preferably less than about 0.012 inch (0.305 mm). The mandrel has a small diameter distal section which extends into the portion of the dilatation catheter which extends out of the distal end of the guiding catheter and into the patient's coronary artery during the angioplasty procedure.

7 Claims, 1 Drawing Sheet

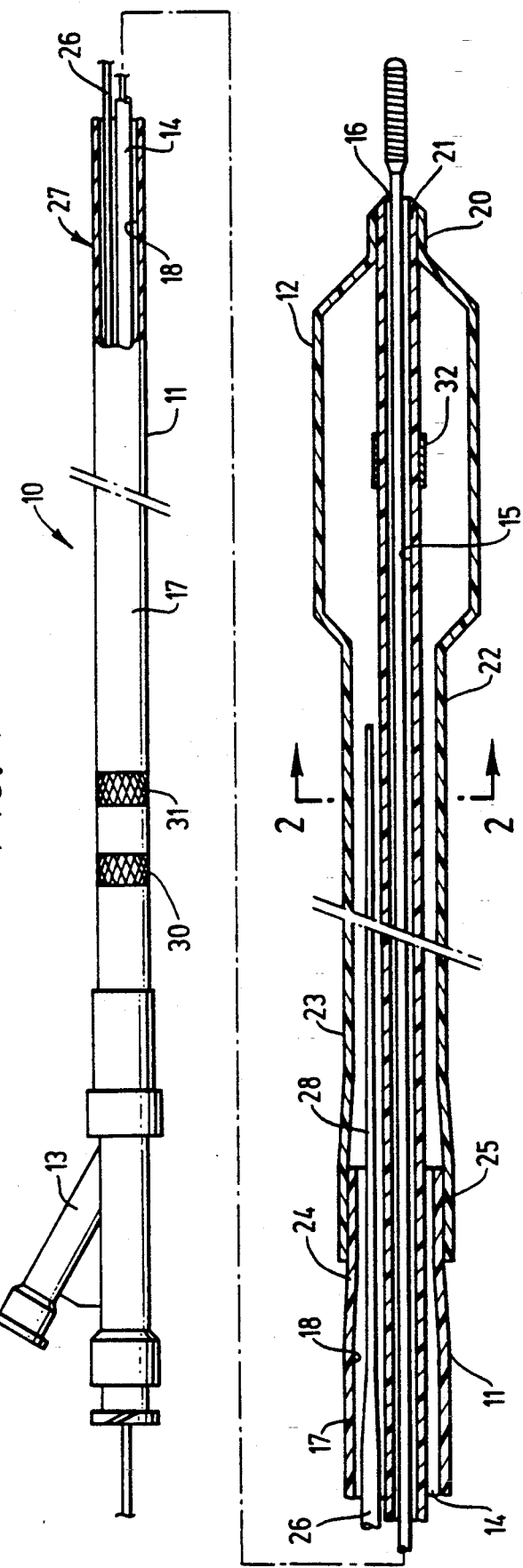

DILATATION CATHETER WITH REINFORCING MANDREL

BACKGROUND OF THE INVENTION

This invention generally relates to dilatation catheters for use in percutaneous transluminal coronary angioplasty (PTCA) procedures and particularly to over-the-wire dilatation catheters for such use.

In classic PTCA procedures, a guiding catheter having a preshaped distal tip is percutaneously introduced into the cardiovascular system of a patient and advanced therein until the preshaped distal tip thereof is disposed within the aorta adjacent the ostium of the desired coronary artery. The guiding catheter is twisted or torqued from its proximal end, which extends outside of the patient, to turn the distal tip of the guiding catheter so that it can be guided into the coronary ostium and seated therein. In an over-the-wire dilatation catheter system, a guidewire is slidably disposed within an inner lumen of the dilatation catheter and the assembled catheter and guidewire are introduced into and advanced through the proximal end of the guiding catheter to the distal tip of the guiding catheter seated within the coronary ostium. The distal tip of the guidewire is usually manually shaped (curved) by the physician or one of the attendants before it is introduced into the guiding catheter along with the dilatation catheter.

The shaped distal tip of the guidewire is first advanced out the distal tip of the guiding catheter into the patient's coronary artery. To guide the curved or otherwise shaped distal end of the guidewire into a targeted branch artery having a stenosis which to be dilated, a torque is applied to the proximal end of the guidewire, which extends out of the proximal end of the guiding catheter, as it is advanced within the coronary anatomy. The advancement of the guidewire within the target artery continues until the distal end of the guidewire crosses the lesion to be dilated.

The dilatation catheter is then advanced out of the distal tip of the guiding catheter into the patient's coronary anatomy, over the previously advanced guidewire, until the balloon on the distal extremity of the dilatation catheter is properly positioned across the stenosis to be dilated. Once properly positioned across the stenosis, the flexible, relatively inelastic dilatation balloon on the dilatation catheter is inflated to a predetermined size with radiopaque liquid at relatively high pressures (e.g., generally 4-12 atmospheres) to dilate the stenosed region of the diseased artery. One or more inflations of the balloon may be required to complete the dilation. After the last dilation, the balloon is deflated so that the dilatation catheter can be removed from the dilated stenosis and blood flow can resume through the dilated artery.

Further details of guiding catheters, dilatation catheters, guidewires, and other devices for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,438,622 (Samson et al.); U.S. Pat. No. 4,554,929 (Samson et al.); U.S. Pat. No. 4,582,185 (Samson); U.S. Pat. No. 4,616,652 (Simpson); U.S. Pat. No. 4,638,805 (Powell); U.S. Pat. No. 4,748,986 (Morrison et al.); U.S. Pat. No. 4,898,577 (Badger et al.); U.S. Pat. No. 4,748,982 (Horzewski et al.) and U.S. Pat. No. 4,821,722 (Miller et al.) which are hereby incorporated herein in their entirety by reference thereto.

On going development work has reduced the transverse dimensions of dilatation catheters for angioplasty procedures both as to their outer diameters as well as the wall thicknesses of the tubular components. This has led to difficulties in designing dilatation catheters having small transverse dimensions with adequate pushability for advancement through guiding catheters, deep into the patient's coronary artery and across tight stenoses. The marginal or inadequate pushability has been particularly noticeable with over-the-wire catheters adapted for use with guidewires having diameters not more than about 0.014 inch (0.356 mm), particularly not more than about 0.012 inch (0.305 mm). What has been needed and heretofore unavailable is a small diameter, thin-walled over-the-wire dilatation catheter which can be pushed through guiding catheters of various distal shapes and deep within a patient's coronary artery over small diameter guidewires with good tracking and distal flexibility. The present invention satisfies this and other needs.

SUMMARY OF THE INVENTION

This invention is directed to a small diameter over-the-wire dilatation catheter which has excellent pushability and which is particularly suitable for dilating distal stenoses within small diameter coronary arteries.

The dilatation catheter of the invention generally has an elongated catheter shaft with an inflatable member on a distal portion thereof and an adapter on the proximal end of the catheter shaft. The catheter shaft has a relatively long proximal portion which usually remains within the guiding catheter during the angioplasty procedure and a relatively short distal portion which usually extends out of the distal end of the guiding catheter into the patient's coronary artery during the angioplasty procedure.

The catheter shaft has an inner tubular member with an inner lumen adapted to receive a guidewire with a maximum OD of less than about 0.014 inch, particularly less than about 0.012 inch and an outer tubular member which is disposed about the inner tubular member and which defines a annular lumen therebetween. The inflatable member has a proximal end which is secured to the distal portion of the outer tubular member and a distal end secured to the distal end of the inner tubular member so as to seal off the annular lumen and the interior of the inflatable member.

A reinforcing mandrel is fixed within the annular lumen between the inner and outer tubular members and extends from the proximal end of the catheter shaft into the distal portion of the catheter shaft but it terminates short of the proximal end of the inflatable member, e.g. at least 5 mm. from the proximal end of the inflatable member, i.e., the proximal end of the proximal taper of the inflatable member. Preferably, the portion of the mandrel which extends into the distal portion of the catheter has smaller transverse dimensions than the proximal portion of the mandrel. The mandrel is fixed within the annular lumen by suitable means such as firmly securing the proximal end of the mandrel within the adapter mounted on the proximal end of the catheter shaft. The small diameter portion of the mandrel which extends into the distal portion of the catheter shaft, preferably has transverse dimensions at least 20% less than the transverse dimension of the proximal portion of the mandrel. This provides flexibility in the distal portion of the catheter and allows the catheter to track over the guidewire while maintaining excellent pushability. These and other advantages of the invention will become more apparent from the following detailed description thereof when taken in conjunction with the accompanying exemplary drawings.

BRIEF DESCRIPTION OF THE DRAWINGS

FIG. 1 is an elevational view, partially in section of a dilatation catheter embodying features of the invention.

FIG. 2 is a cross sectional view taken along the lines 2—2 shown in FIG. 1.

DETAILED DESCRIPTION OF THE INVENTION

Reference is made to FIGS. 1 and 2 which depict a dilatation catheter 10 for angioplasty procedures embodying features of the invention. The catheter 10 generally includes an elongated catheter shaft 11 with an inflatable balloon 12 on the distal portion thereof and an adapter 13 on the proximal end thereof. The catheter shaft 11 has an inner tubular member 14 which has a inner lumen 15 which is adapted to receive a guidewire with an OD of about 0.014 inch or less and which extends therein to the distal guidewire port 16 in the distal end of the inner tubular member. An outer tubular member 17 is disposed about the inner tubular member 14 and defines an annular lumen 18 with the inner tubular member. The distal end 20 of the inflatable balloon 12 is suitably bonded to the distal end 21 of the inner tubular member 14 so as to seal the interior of the balloon 12 and the annular lumen 18. The proximal end 22 of the balloon 12 has an elongated waist 23 which is bonded to the distal end 24 of the outer tubular member 17 by means of a suitable heat bond or adhesive in a lap joint 25.

Reinforcing mandrel 26, which is fixed within the annular lumen 18, has a relatively long proximal section 27 having a relatively large outer diameter and a relatively short distal section 28 which has a relatively small outer diameter. The small diameter distal section 28 extends through the distal portion of the catheter but terminates short of the proximal end 22 of the balloon 12. The small diameter tapered section 28 preferably begins proximal to the lap joint 25 between the proximal waist 23 of the balloon 12 because the size of the annular lumen 18 may be reduced somewhat under the lap joint 25. To fix the mandrel 26 within the inner annular lumen 18, the proximal end of the mandrel is preferably flattened and secured within the adapter 13 by suitable means (not shown) such as a heat shrink tube or an adhesive. Most, if not all, of the small diameter distal section 28 of the mandrel 26 is disposed within the most distal 20-30 cm of the dilatation catheter which is the portion of the catheter which extends out of the distal end of the guiding catheter into the patient's coronary artery during the angioplasty procedure. While the distal small diameter section 28 of the mandrel 26 is shown in FIG. 1 as having a single sized diameter, several sections which have sequentially smaller diameters (sequential in the distal direction) can be provided with tapers between the various sized sections. The diameter of the proximal section of the mandrel ranges from about 0.013 to about 0.008 inch (0.33–0.20 mm) and the diameter of the distal section ranges from about 0.008 to about 0.004 inch (0.20–0.10 mm). The overall length of the mandrel is about 100 to about 134.5 cm with the small diameter distal portion thereof being about 10 to about 25 cm in length.

Typical dimension in one presently preferred embodiment of the invention include an inner tubular member with an ID of about 0.014 inch (0.356 mm), and OD of about 0.020 inch (0.51 mm) and an outer tubular member with an ID of about 0.03 inch (0.76 mm) and an OD of about 0.038 inch (0.97 mm). This particular embodiment was adapted to receive a guidewire having an OD of about 0.01 inch (0.25 mm). The proximal balloon waist can range from about 15 to about 25 cm. Other dimensions of the catheter may be conventional.

Visual markers 30 and 31 are provided on the proximal portion of the shaft 11 and radiopaque marker 32 is provided on the inner tubular member 15 at the midpoint of the balloon 12 in order to facilitate fluoroscopic observation of the catheter within the patient.

The various components of the catheter can be made from conventional materials. The inner and outer tubular members can be made from a mixture of high density and low density polyethylene, the inflatable member or balloon from polyethylene, polyethylene terephthalate, polyolefenic ionomers such as Surlyn ®, sold by the Dupont Company, and polyvinyl chloride. Also suitable is the balloon construction disclosed in copending application Ser. No. 07/758,630, filed Sep. 12, 1991, entitled FORMED IN PLACE BALLOONS FOR VASCULAR CATHETERS. The mandrel can be made of stainless steel, superelastic NiTi alloys or other suitable materials such as high strength plastic. The tapers and small diameter portions of the mandrel can be formed in the same manner as that used for forming small diameter sections on guidewires, e.g. centerless grinding. Plastic-to-plastic or plastic-to-metal joints can be effected by suitable adhesives such as cyanoacrylate sold under the trademark Loctite, e.g. Loctite 405.

While the present invention has been described herein primarily in terms of certain preferred embodiments, those skilled in the art will recognize that various modifications and improvements can be made without departing from the scope thereof.

What is claimed is:

1. A dilatation catheter for performing angioplasty procedures within a patient's coronary artery having a relatively long proximal section which is adapted to remain within a guiding catheter during the angioplasty procedure and a relatively short distal section which is adapted to extend out of the distal end of the guiding catheter during the angioplasty procedure, the dilatation catheter comprising:

a) an elongated catheter shaft which includes an elongated inner tubular member which has a distal end, a distal guidewire port in the distal end and a guidewire receiving inner lumen extending within the inner tubular member to the distal guidewire port in the distal end and an elongated outer tubular member which is disposed about the inner tubular member and defines therewith an annular lumen;

b) an inflatable member on a distal portion of the catheter shaft having a distal end secured to the distal end of the inner tubular member and an interior which is in fluid communication with the annular lumen between the inner and outer tubular members;

c) a reinforcing mandrel disposed within the annular lumen between the inner and outer tubular members which has a relatively long proximal section and a relatively short, distal section which has a smaller diameter than the diameter of the proximal section and which extends into the distal portion of the catheter but terminating proximal to the inflatable member.

2. The dilatation catheter of claim 1 including a guidewire having an OD of not more than about 0.012 inch slidably disposed within the inner lumen of the inner tubular member.

3. The dilatation catheter of claim 1 including a guidewire having an OD of not more than about 0.012 inch slidably disposed within the inner lumen of the inner tubular member.

4. The dilatation catheter of claim 1 wherein the proximal section of the mandrel has an OD from about 0.008 to about 0.013 inch and the distal section of the mandrel has an OD smaller than the OD of the proximal section and ranging from about 0.004 to about 0.008 inch.

5. The dilatation catheter of claim 1 wherein the catheter has a proximal end and the mandrel is secured within an adapter mounted on the proximal end of the catheter.

6. The dilatation catheter of claim 1 wherein the mandrel has a distal end which is spaced at least 5 mm from the proximal end of the inflatable member.

7. The dilatation catheter of claim 1 wherein the inflatable member is a balloon formed of relatively inelastic material.

* * * * *